United States Patent
Takahashi

(10) Patent No.: US 12,329,356 B2
(45) Date of Patent: Jun. 17, 2025

(54) OVERTUBE WITH TUBE MAIN BODY, GRIPPING CYLINDER HAVING OBLIQUELY EXTENDED CONNECTING PIPES, AND BALLOON

(71) Applicant: FUJIFILM Corporation, Tokyo (JP)

(72) Inventor: Nobuharu Takahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 883 days.

(21) Appl. No.: 17/161,679

(22) Filed: Jan. 29, 2021

(65) Prior Publication Data

US 2021/0145258 A1    May 20, 2021

Related U.S. Application Data

(63) Continuation of application No. PCT/JP2019/030256, filed on Aug. 1, 2019.

(30) Foreign Application Priority Data

Sep. 4, 2018 (JP) ................. 2018-165190

(51) Int. Cl.
*A61B 1/00* (2006.01)
*A61B 1/005* (2006.01)
*A61M 25/10* (2013.01)

(52) U.S. Cl.
CPC ...... *A61B 1/00135* (2013.01); *A61B 1/00066* (2013.01); *A61B 1/00082* (2013.01); *A61B 1/005* (2013.01); *A61M 2025/1061* (2013.01)

(58) Field of Classification Search
CPC ............ A61B 1/00135; A61B 1/00066; A61B 1/00082; A61B 1/0052; A61B 1/01;
(Continued)

(56) References Cited

U.S. PATENT DOCUMENTS

2003/0135091 A1  7/2003 Nakazawa et al.
2004/0082938 A1  4/2004 Ohyama et al.
(Continued)

FOREIGN PATENT DOCUMENTS

EP  2368482        9/2011
EP  2368482 A1 *   9/2011  ......... A61B 1/00105
(Continued)

OTHER PUBLICATIONS

"International Search Report (Form PCT/ISA/210) of PCT/JP2019/030256," mailed on Sep. 10, 2019, with English translation thereof, pp. 1-5.
(Continued)

*Primary Examiner* — John P Leubecker
*Assistant Examiner* — Li-Ting Song
(74) *Attorney, Agent, or Firm* — JCIPRNET

(57) ABSTRACT

Provided is an overtube that can be easily gripped by the operator. The overtube includes a tube main body, a gripping cylinder connected to the proximal end side of the tube main body, a balloon mounted on an outer peripheral surface on a distal end side of the tube main body, and an air supply pipe line that is arranged to be parallel to an endoscope insertion passage from the tube main body to the gripping cylinder and communicates with the balloon. The gripping cylinder includes a first connecting pipe that extends obliquely outward from a first position of a gripping cylinder side portion toward the proximal end side of the gripping cylinder, and a second connecting pipe that extends obliquely outward from a second position different from the first position toward the proximal end side of the gripping
(Continued)

cylinder. The gripping cylinder is an integrally molded body in which the first connecting pipe and the second connecting pipe are integrally molded. In a case where the plane orthogonal to the center axis of the gripping cylinder is defined as a first surface, and the plane orthogonal to the first surface and intersecting the air supply pipe line is defined as a second surface, the first position and the second position are disposed on the same side with respect to the reference surface orthogonal to the first surface and orthogonal to the second surface.

20 Claims, 14 Drawing Sheets

(58) Field of Classification Search
CPC ........... A61B 1/00137; A61B 1/00154; A61M 2025/1061; A61M 25/10; A61M 25/01; A61M 2025/018; A61M 25/0136; A61M 2025/09116; A61M 25/0662
USPC .......................................................... 600/115
See application file for complete search history.

(56) References Cited

U.S. PATENT DOCUMENTS

| | | | | |
|---|---|---|---|---|
| 2005/0215855 | A1* | 9/2005 | Machida | A61B 1/00082 600/156 |
| 2008/0249358 | A1* | 10/2008 | Motai | A61B 1/2736 600/115 |
| 2009/0234188 | A1* | 9/2009 | Matsuura | A61B 1/012 600/115 |
| 2009/0318798 | A1* | 12/2009 | Singh | A61B 1/012 604/544 |
| 2013/0267777 | A1* | 10/2013 | Avitsian | A61B 1/00066 600/123 |
| 2015/0065807 | A1* | 3/2015 | Greenberg | A61B 1/05 600/207 |
| 2018/0000325 | A1* | 1/2018 | Okaniwa | A61B 1/0051 |
| 2018/0140445 | A1* | 5/2018 | Geusen | A61F 2/07 |
| 2018/0153376 | A1* | 6/2018 | Begg | A61B 1/00091 |
| 2020/0315426 | A1* | 10/2020 | Yoshinaga | A61B 1/0055 |
| 2020/0353205 | A1* | 11/2020 | Kelly | A61M 39/223 |
| 2020/0405128 | A1* | 12/2020 | Kaffes | A61M 25/0133 |
| 2021/0154443 | A1* | 5/2021 | Casey | A61M 25/0102 |
| 2021/0298579 | A1* | 9/2021 | Matsushita | A61B 1/00082 |
| 2023/0210355 | A1* | 7/2023 | Yamaya | A61B 1/00101 600/133 |
| 2023/0397796 | A1* | 12/2023 | Matsushita | A61B 1/0004 |
| 2024/0016372 | A1* | 1/2024 | Sato | A61B 1/01 |

FOREIGN PATENT DOCUMENTS

| | | |
|---|---|---|
| JP | 2003204920 | 7/2003 |
| JP | 2003299671 | 10/2003 |
| JP | 2008136740 | 6/2008 |
| JP | 2008253780 | 10/2008 |
| JP | 2011200403 | 10/2011 |
| JP | 2012500710 | 1/2012 |
| WO | 2010024801 | 3/2010 |
| WO | 2017090667 | 6/2017 |

OTHER PUBLICATIONS

"Written Opinion of the International Searching Authority (Form PCT/ISA/237) of PCT/JP2019/030256," mailed on Sep. 10, 2019, with English translation thereof, pp. 1-7.

* cited by examiner

OVERTUBE WITH TUBE MAIN BODY, GRIPPING CYLINDER HAVING OBLIQUELY EXTENDED CONNECTING PIPES, AND BALLOON

CROSS-REFERENCE TO RELATED APPLICATIONS

The present application is a Continuation of PCT International Application No. PCT/JP2019/030256 filed on Aug. 1, 2019 claiming priority under 35 U.S.C. § 119(a) to Japanese Patent Application No. 2018-165190 filed on Sep. 4, 2018. Each of the above applications is hereby expressly incorporated by reference, in its entirety, into the present application.

BACKGROUND OF THE INVENTION

1. Field of the Invention

The present invention relates to an overtube comprising an endoscope insertion passage capable of inserting an endoscope.

2. Description of the Related Art

In the medical field, endoscopes are inserted into a bent intestinal tract such as the small and large intestines, and are used for procedures such as observation, diagnosis, and treatment of an inner wall surface. Since an intestinal tract is bent in a complicated manner, the insertion force is not transmitted from an insertion part of the endoscope to a distal end portion, and it is difficult for the distal end portion to advance forward. Furthermore, insertion into a deep portion of the small intestine or into a postoperative patient by the Roux-en-Y method, and the like due to extraction of the stomach, and the like often results in so-called "difficult insertion case" in which the distal end portion does not advance further.

It has been proposed to use an overtube with a balloon (also referred to as insertion aids) in combination with an endoscope to eliminate the difficult insertion case (for example, refer to JP2008-136740A).

SUMMARY OF THE INVENTION

However, in the overtube disclosed in JP2008-136740A, since a liquid supply path and a gas supply and discharge path are disposed substantially symmetrically with respect to an axis of the overtube on the proximal end side, there is a problem that it is difficult for an operator to grip the proximal end of the overtube.

The present invention has been made in view of such circumstances, and an object of the present invention is to provide an overtube that can be easily gripped by an operator.

The overtube according to the first aspect is an overtube having an endoscope insertion passage capable of inserting an endoscope, the overtube comprising a tube main body that is formed with a first insertion passage constituting a part of the endoscope insertion passage, a gripping cylinder that is connected to a proximal end side of the tube main body and is formed with a second insertion passage constituting another part of the endoscope insertion passage, a balloon that is mounted to an outer peripheral surface on a distal end side of the tube main body, and an air supply pipe line that is arranged to be parallel to the endoscope insertion passage from the tube main body to the gripping cylinder and communicates with the balloon, in which the gripping cylinder includes a first connecting pipe that has a gas pipe line extending obliquely outward from a first position of a gripping cylinder side portion between the proximal end and the distal end of the gripping cylinder toward the proximal end side of the gripping cylinder, and communicating with the air supply pipe line, and a second connecting pipe that has a liquid pipe line extending obliquely outward from a second position different from the first position of the gripping cylinder side portion toward the proximal end side of the gripping cylinder and communicating with the second insertion passage, the gripping cylinder is an integrally molded body that the first connecting pipe and the second connecting pipe are integrally molded, and in a case where a plane surface orthogonal to a center axis of the gripping cylinder is defined as a first surface, and a plane surface orthogonal to the first surface and intersecting the air supply pipe line is defined as a second surface, the first position and the second position are disposed on the same side with respect to a reference surface orthogonal to the first surface and orthogonal to the second surface. According to the first aspect, the operator can easily grip the gripping cylinder of the overtube.

The overtube according to the second aspect is an overtube having an endoscope insertion passage through which an endoscope can be inserted, the overtube comprising a tube main body in which a first insertion passage constituting a part of the endoscope insertion passage is formed a gripping cylinder that is connected to a proximal end side of the tube main body, in which a second insertion passage constituting another part of the endoscope insertion passage is formed, a balloon that is mounted to an outer peripheral surface on a distal end side of the tube main body, and an air supply pipe line that is arranged to be parallel to the endoscope insertion passage from the tube main body to the gripping cylinder and communicates with the balloon, in which the gripping cylinder includes a first connecting pipe that extends obliquely outward from a first position of a gripping cylinder side portion between a proximal end and a distal end of the gripping cylinder toward the proximal end of the gripping cylinder, and has a gas pipe line communicating with the air supply pipe line, and a second connecting pipe that extends obliquely outward from a second position different from the first position of the gripping cylinder side portion toward the proximal end side of the gripping cylinder and has a liquid pipe line communicating with the second insertion passage, the gripping cylinder is an integrally molded body in which the first connecting pipe and the second connecting pipe are integrally molded, and as viewed from an axial direction of a center axis of the gripping cylinder, an angle formed by a first straight line connecting the center axis and the first position and a second straight line connecting the center axis and the second position is an acute angle or 0 degrees. According to the second aspect, the operator can easily grip the gripping cylinder of the overtube.

In the overtube of the third aspect, the gripping cylinder side portion has a flange-shaped stopper formed to extend outward from an inside in a radial direction of the center axis of the gripping cylinder, and the first position and the second position are positioned on a surface of the proximal end side of the stopper. According to the third aspect, since the stopper of the overtube is in contact with a mouthpiece held by the subject, the position of the overtube with respect to the subject can be fixed.

In the overtube according to the fourth aspect, the gripping cylinder side portion has a relay pipe line that forms a part of the air supply pipe line and communicates with the gas pipe line, and the gas pipe line and the relay pipe line are bent and connected. According to the fourth aspect, since it is possible to extend from the first position to the outside without being affected by the relay pipe line of the first connecting pipe formed with the gas pipe line, the degree of freedom in designing the gripping cylinder can be increased.

In the overtube according to the fifth aspect, the gas pipe line is provided so as to be inclined obliquely outward toward the proximal end side of the gripping cylinder from the relay pipe line. According to the fifth aspect of the present invention, since the first connecting pipe formed with the gas pipe line is inclined obliquely outward and the first connecting pipe is spaced from the gripping cylinder side portion, the operator can more easily grip the gripping cylinder of the overtube.

In the overtube of the sixth aspect, in a case where the plane orthogonal to the center axis of the gripping cylinder is defined as the first surface, and the plane orthogonal to the first surface and intersecting the air supply pipe line is defined as the second surface, an angle of a pipe line axis of the gas pipe line with respect to the reference surface orthogonal to the first surface and orthogonal to the second surface is 40 degrees or less. According to the sixth aspect, by setting the angle of the pipe line axis of the gas pipe line to 40 degrees or less, the gas pipe line can be easily molded.

In the overtube of the seventh aspect, in a case where the first connecting pipe and the second connecting pipe are projected on the plane orthogonal to the center axis of the gripping cylinder, regions of at least parts of the first connecting pipe and the second connecting pipe overlap each other. According to the seventh aspect, the gripping cylinder can be miniaturized by bringing the first connecting pipe and the second connecting pipe close to each other.

In the overtube of the eighth aspect, the first position and the second position are at the same position in a circumferential direction of the center axis of the gripping cylinder. According to the eighth aspect, the gripping cylinder can be miniaturized by bringing the first position and the second position closer to each other.

In the overtube according to the ninth aspect, in a case where a distance between the center axis of the gripping cylinder and the first position is defined as a first distance and a distance between the center axis of the gripping cylinder and the second position is defined as a second distance, the first distance is larger than the second distance.

In the overtube of the tenth aspect, the second connecting pipe is provided between the first connecting pipe and the gripping cylinder.

According to the ninth aspect or the tenth aspect, since the air supply pipe line is not blocked by the liquid pipe line, the air supply pipe line can be arranged to be parallel to the balloon along the tube main body.

In the overtube of the eleventh aspect, the first position and the second position are positions closer to the proximal end of the gripping cylinder than the distal end of the gripping cylinder. According to the eleventh aspect, the length of the overtube that can be inserted into the body cavity of the subject can be increased.

The overtube of the twelfth aspect is an overtube having an endoscope insertion passage through which an endoscope can be inserted, the overtube comprising a tube main body in which a first insertion passage constituting a part of the endoscope insertion passage is formed, a gripping cylinder that is connected to a proximal end side of the tube main body, in which a second insertion passage constituting another part of the endoscope insertion passage is formed, a balloon that is mounted to an outer peripheral surface on a distal end side of the tube main body, and an air supply pipe line that is arranged to be parallel to the endoscope insertion passage from the tube main body to the gripping cylinder and communicates with the balloon, in which the gripping cylinder includes a first connecting pipe that extends obliquely outward from a first position of a gripping cylinder side portion between a proximal end and a distal end of the gripping cylinder toward the proximal end side of the gripping cylinder, and has a gas pipe line communicating with the air supply pipe line, and a second connecting pipe that extends obliquely outward from a second position different from the first position of the gripping cylinder side portion toward the proximal end side of the gripping cylinder and has a liquid pipe line communicating with the second insertion passage, the gripping cylinder is an integrally molded body in which the first connecting pipe and the second connecting pipe are integrally molded, the gripping cylinder side portion has a flange-shaped stopper formed to extend outward from an inside in a radial direction of a center axis of the gripping cylinder, and the first position and the second position are positions on the stopper or between the proximal end of the gripping cylinder and the stopper. According to the twelfth aspect, the length of the overtube that can be inserted into the body cavity of the subject can be increased.

In the overtube of the thirteenth aspect, in the gas pipe line and the liquid pipe line of the gripping cylinder, the gas pipe line is disposed at a position outside the liquid pipe line with respect to the center axis of the gripping cylinder. According to the thirteenth aspect, it is possible to place the tube from the apparatus for supplying air into the balloon at a position where the tube is not obstructed in a case where the operator holds the gripping cylinder.

According to the present invention, the operator can easily grip the gripping cylinder of the overtube.

DESCRIPTION OF THE PREFERRED EMBODIMENTS

First Embodiment

Figure 1:
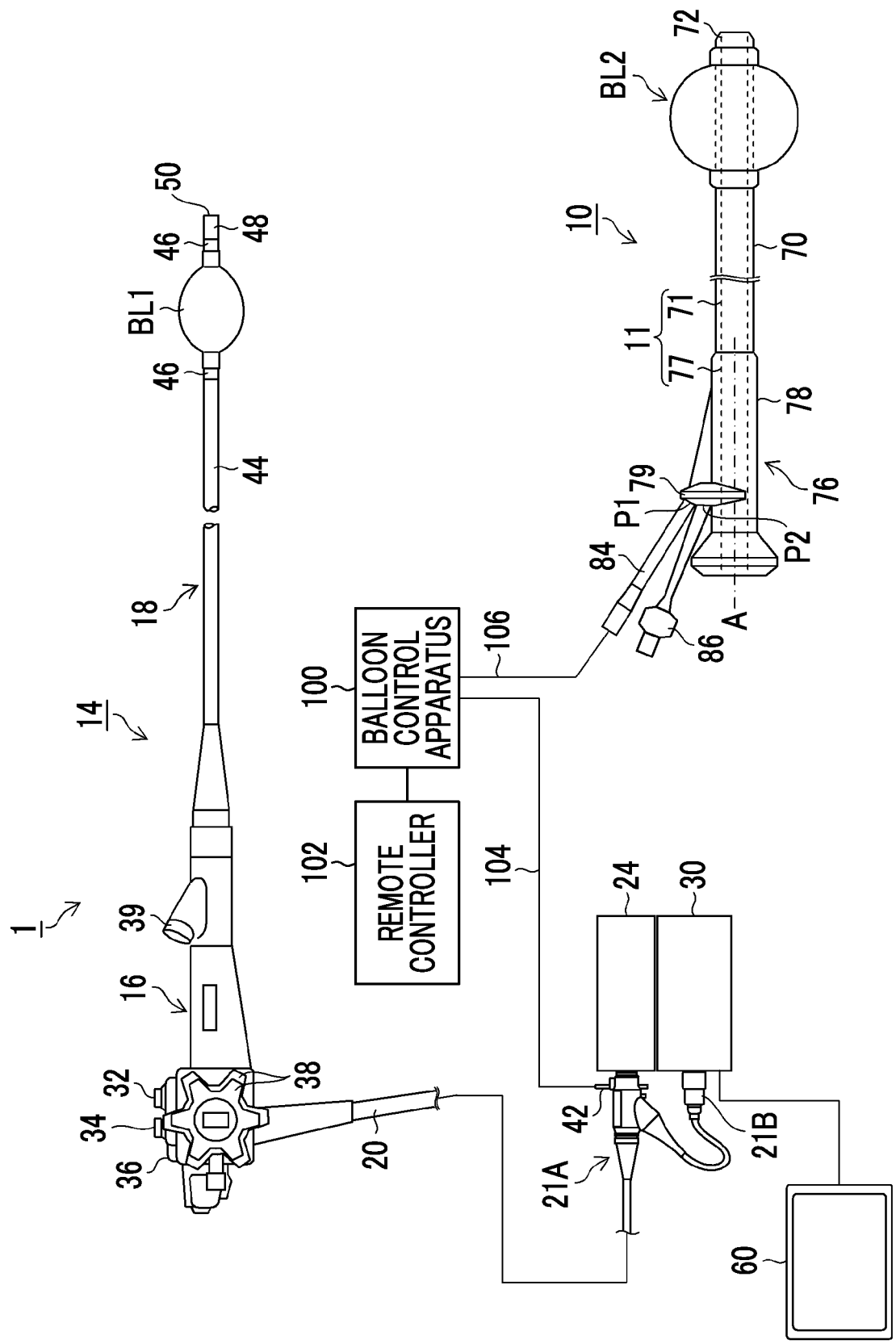
FIG. 1 is a system configuration view of an endoscope apparatus.

An overtube of the first embodiment will be described with reference to the drawings. FIG. 1 is a system configuration view of an endoscope apparatus 1. As shown in FIG. 1, the endoscope apparatus 1 comprises a flexible endoscope 14, an overtube 10, a balloon control apparatus 100, and the like.

The endoscope 14 comprises a hand operation portion 16 and an insertion part 18 which is provided at the hand operation portion 16. A universal cable 20 is connected to the hand operation portion 16. The universal cable 20 includes a signal cable (not shown), a light guide (not shown), an air supply tube (not shown), and the like. A connector 21A and a connector 21B are provided at a distal end of the universal cable 20. The connector 21A is connected to a light source apparatus 24. The connector 21B is branched from the connector 21A and connected to a processor 30. A monitor 60 is connected to the processor 30.

The connector 21A is provided with a balloon air supply port 42. The balloon air supply port 42 supplies air to the inside of the first balloon BL1 and sucks air from the inside of the first balloon BL1. It should be noted that the term "air" as used herein is a gas for inflating the first balloon BL1 (including the second balloon BL2 described later), and the type (component) thereof is not particularly limited. The balloon air supply port 42 is connected to the balloon control apparatus 100 via a tube 104.

In addition, in the hand operation portion 16, an air supply and water supply button 32, a suction button 34, and a shutter button 36 are arranged to be parallel, and a pair of angle knobs 38 and a treatment tool insertion part 39 are provided.

The insertion part 18 is inserted into the intestinal tract such as the small intestine and the large intestine. The insertion part 18 is configured by a flexible portion 44, a curved portion 46, and a distal end portion 48 from a proximal end side toward a distal end side.

The flexible portion 44 is provided at the proximal end of the curved portion 46 and has flexibility. The curved portion 46 is remotely bent (angle operation) by operating a pair of angle knobs 38 provided at the hand operation portion 16. The pair of angle knobs 38 can direct a distal end surface 50 of the distal end portion 48 in a desired direction.

In addition, the first balloon BL1 is mounted to an outer peripheral surface of the curved portion 46. The balloon air supply port 42 is connected to an air supply tube inserted into the insertion part 18 and the connector 21A. In the air supply tube, a ventilation hole (not shown) is opened on the distal end side thereof. The ventilation hole is open inside the first balloon BL1. The ventilation hole allows the supply and suction of gas to the first balloon BL1. Air is blown from the ventilation hole into the first balloon BL1 to inflate the first balloon BL1, and air in the first balloon BL1 is sucked from the ventilation hole to contract the first balloon BL1. Although the endoscope 14 comprising the first balloon BL1 on the outer peripheral surface of the curved portion 46 has been exemplified, the endoscope 14 does not have to be provided with the first balloon BL1.

Figure 2:
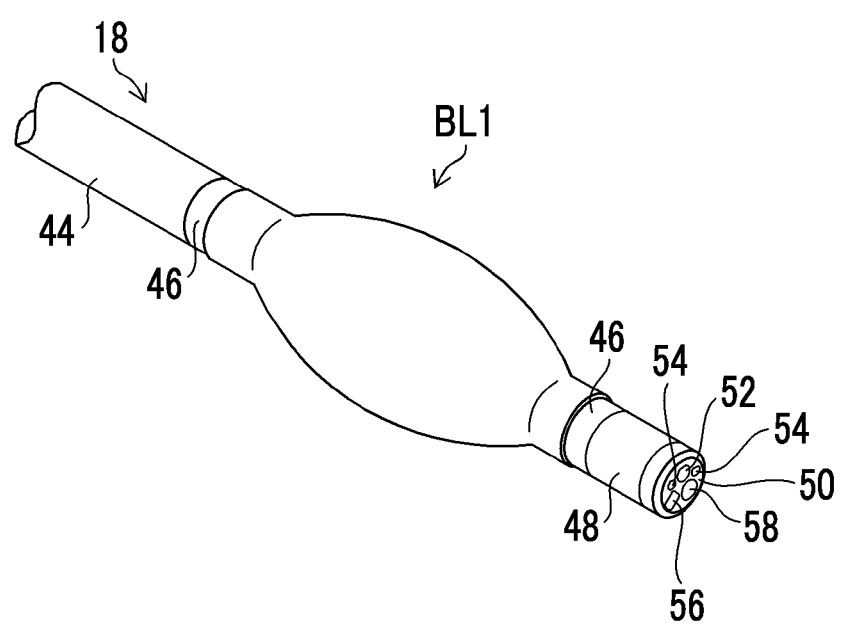
FIG. 2 is an enlarged perspective view of a distal end portion of the insertion part.

FIG. 2 is an enlarged perspective view of the distal end portion 48 of the insertion part 18. As shown in FIG. 2, the distal end surface 50 of the distal end portion 48 is provided with an observation window 52, a pair of illumination windows 54, an air supply and water supply nozzle 56, and a forceps port 58. In the distal end portion 48, an imaging element (not shown) is provided behind the observation window 52. An observation image is formed on the imaging element and is photoelectrically converted. A signal cable (not shown) is connected to the imaging element, and the signal cable is connected to the processor 30 via the insertion part 18, the hand operation portion 16, and the universal cable 20, which are described above. Therefore, the imaging signal of the observation image photoelectrically converted by the imaging element is output to the processor 30, and then is output to the monitor 60 (refer to FIG. 1) after the signal is appropriately processed in the processor. Accordingly, the observation image is displayed on the monitor 60.

A light emitting end of the light guide (not shown) is disposed behind each of the pair of illumination windows 54 in the distal end portion 48. A light incident end of each light guide is connected to the light source apparatus 24. Accordingly, an observed part is irradiated with illumination light supplied from the light source apparatus 24 to the light incident end of each light guide through the pair of illumination windows 54.

Returning to FIG. 1, the overtube 10 has a tube main body 70 and a gripping cylinder 76 connected to the proximal end side of the tube main body 70. The overtube 10 has a tubular structure for forming an endoscope insertion passage 11 through which the insertion part 18 of the endoscope 14 can be inserted. An inner surface of the overtube 10 forms the endoscope insertion passage 11. The endoscope insertion passage 11 of the overtube 10 has an inner diameter slightly larger than the outer diameter of the insertion part 18. The endoscope insertion passage 11 allows the insertion part 18 to move forward and backward inside the overtube 10, facilitating the procedure by the endoscope 14.

The tube main body 70 is made of various flexible materials in a tubular shape. By forming a tubular shape, the first insertion passage 71 is formed in the tube main body 70. The first insertion passage 71 constitutes a part of the endoscope insertion passage 11. A second balloon BL2 formed of various elastic bodies is provided on the outer peripheral surface of the tube main body 70 on the distal end side.

The gripping cylinder 76 connected to the proximal end side of the tube main body 70 is formed in a tubular shape by various hard materials. By forming a tubular shape, the second insertion passage 77 is formed in the gripping cylinder 76. The second insertion passage 77 constitutes the other part of the endoscope insertion passage 11. The gripping cylinder 76 has a center axis A. The center axis A is a virtual axis extending along the longitudinal direction of the gripping cylinder 76 and passing through the center of the second insertion passage 77.

The gripping cylinder 76 comprises the first connecting pipe 84 extending obliquely outward from the first position P1 of a gripping cylinder side portion 78 between the proximal end and the distal end of the gripping cylinder 76 toward the proximal end side of the gripping cylinder 76. As will be described later, the first connecting pipe 84 is formed in a tubular shape. The first connecting pipe 84 has a gas pipe line 91 communicating with an air supply pipe line 12 (refer to FIG. 3). The inner surface of the first connecting pipe 84 forms the gas pipe line 91. The first connecting pipe 84 is connected to the balloon control apparatus 100 via a tube 106.

The gripping cylinder 76 comprises the second connecting pipe 86 extending obliquely outward from the second position P2 different from the first position P1 of the gripping cylinder side portion 78 toward the proximal end side of the gripping cylinder 76. Unless the first position P1 and the second position P2 completely match, the first position P1 and the second position P2 are different positions. As will be described later, the second connecting pipe 86 is formed in a tubular shape. The second connecting pipe 86 has a liquid pipe line 92 communicating with the second insertion passage 77 (refer to FIG. 3). The inner surface of the second connecting pipe 86 forms the liquid pipe line 92. Although not shown, a lubricant supply portion such as a syringe is connected to the second connecting pipe 86.

The gripping cylinder 76 is an integrally molded body in which the first connecting pipe 84 and the second connecting pipe 86 are integrally molded. On the basis of Japanese Industrial Standard JISK-7010, integral molding means integrally molding products (molded body) at the same time as joining members without using secondary bonding or mechanical joining.

The gripping cylinder side portion 78 preferably has a flange-shaped stopper 79 formed so as to extend outward from the inside in the radial direction of the center axis A of the gripping cylinder 76. The flange-shaped means a form in which the outer peripheral surface of the gripping cylinder side portion 78 of the gripping cylinder 76 protrudes. The first position P1 and the second position P2 are positioned on the surface of the stopper 79 on the proximal end side. The stopper 79 is in contact with the mouthpiece as described later. The stopper 79 and the mouthpiece fix the position of the overtube with respect to the subject. In addition, the stopper 79 serves to reinforce the first connecting pipe 84 extending from the first position P1 and the second connecting pipe 86 extending from the second position P2. Since the stopper 79 thickness a root portion of the first connecting pipe 84 and the second connecting pipe 86, the damage resistance of the first connecting pipe 84 and the second connecting pipe 86 is improved.

Figure 3:
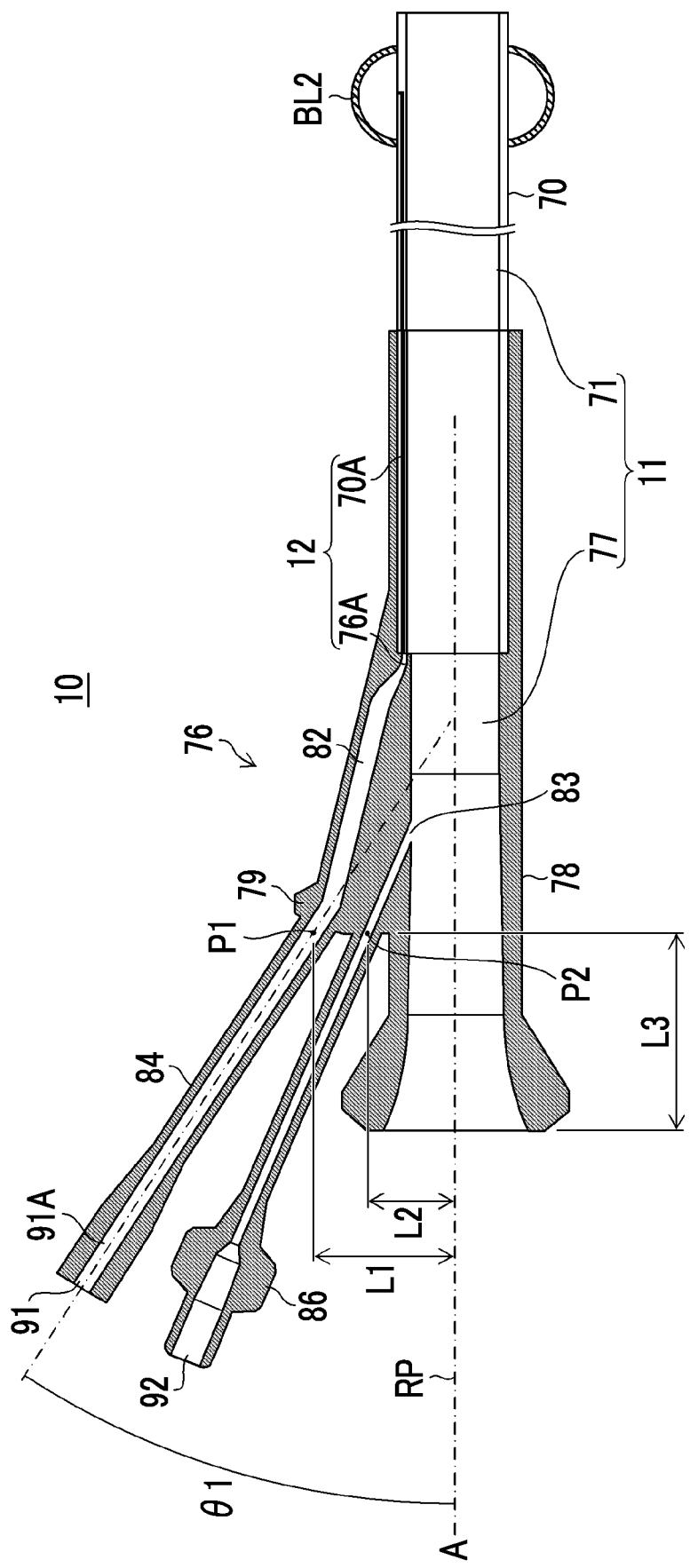
FIG. 3 is a cross-sectional view taken along a center axis of an overtube.
Figure 4:
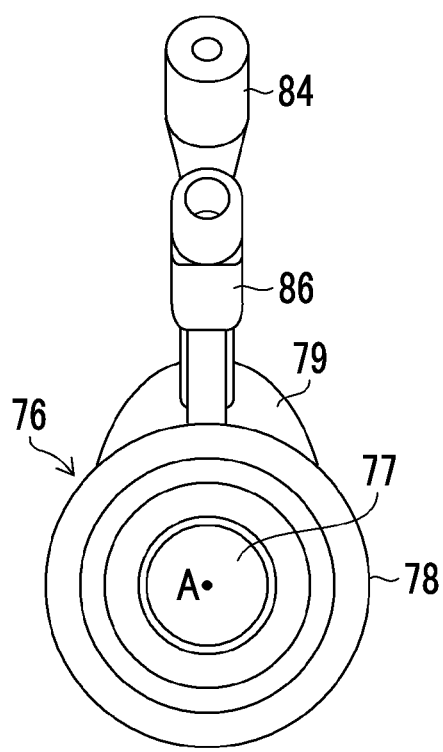
FIG. 4 is a view of the overtube of FIG. 3 viewed from a proximal end side along a center axis.

The overtube 10 will be described on the basis of FIG. 3 and FIG. 4. FIG. 3 is a cross-sectional view taken along the center axis A of the gripping cylinder 76 and cut along a cutting line passing through the first connecting pipe 84 and the second connecting pipe 86. FIG. 4 is a view of the overtube 10 viewed from a proximal end side along the center axis A. As described above, the gripping cylinder 76 comprises the second insertion passage 77, the stopper 79, the first connecting pipe 84 and the second connecting pipe 86 in which the gripping cylinder side portion 78 extends outward.

As shown in FIG. 3, the overtube 10 comprises the air supply pipe line 12 communicating with the second balloon BL2. The air supply pipe line 12 is arranged to be parallel to the endoscope insertion passage 11 from the tube main body 70 to the gripping cylinder 76. The second balloon BL2 inflates in a case where air is blown into the inside of the second balloon BL2 via the air supply pipe line 12. The air inside the second balloon BL2 is sucked via the air supply pipe line 12 to contract the second balloon BL2.

The first connecting pipe 84 has a gas pipe line 91 communicating with an air supply pipe line 12. It is preferable that the gripping cylinder side portion 78 constitutes a part of the air supply pipe line 12 and has a relay pipe line 82 communicating with the gas pipe line 91. The relay pipe line 82 communicates with the gas pipe line 91. The air supply pipe line 12 includes a portion of a pipe line 70A formed between an outer peripheral surface and an inner peripheral surface of the tube main body 70, a portion of a pipe line 76A formed inside the gripping cylinder 76, and the relay pipe line 82 formed on the gripping cylinder side portion 78.

In addition, it is preferable that the gas pipe line 91 and the relay pipe line 82 are preferably bent and connected. Being bent and connected means that the gas pipe line 91 and the relay pipe line 82 are not in a straight line but are bent. This bent connection makes it possible to select the extending direction of the gas pipe line 91 without being affected by the extending direction of the relay pipe line 82. Accordingly, since the direction of the first connecting pipe 84 forming the gas pipe line 91 can be freely selected, the gripping cylinder 76 can secure a degree of freedom in design.

In addition, it is preferable that the gas pipe line 91 is provided so as to be inclined obliquely outward from the relay pipe line 82 toward the proximal end side of the gripping cylinder 76. Since the first connecting pipe 84 having the gas pipe line 91 is inclined outward, the operator can easily grip the gripping cylinder 76. Oblique outward inclination means that in a case where an extended line of the relay pipe line 82 extended to the proximal end side is compared with the gas pipe line 91, the gas pipe line 91 is located at a position gradually separated from the gripping cylinder side portion 78 to the proximal end side from the extended line.

The second connecting pipe 86 has a liquid pipe line 92 communicating with the second insertion passage 77. The liquid pipe line 92 is a pipe line for supplying a lubricant such as water between the inner peripheral surface of the overtube 10 and the outer peripheral surface of the insertion part 18 (not shown). For example, from a syringe connected to the second connecting pipe 86, the lubricant such as water is supplied to the liquid pipe line 92 via the second insertion passage 77. The lubricant reduces friction between the overtube 10 and the insertion part 18 inserted into the overtube 10. A liquid pipe line 83 is formed inside the gripping cylinder 76, and the liquid pipe line 92 and the liquid pipe line 83 of the second connecting pipe 86 communicate with each other.

As shown in FIG. 3, with respect to the first position P1 and the second position P2, the first distance L1 to the first position P1 is longer than the second distance L2 to the second position P2 with the center axis A as a reference, and the distance L3 from the proximal end is equal with the proximal end of the gripping cylinder 76 as a reference. The first position P1 and the second position P2 are disposed in parallel along the radial direction with the center axis A as a reference.

Figure 5:
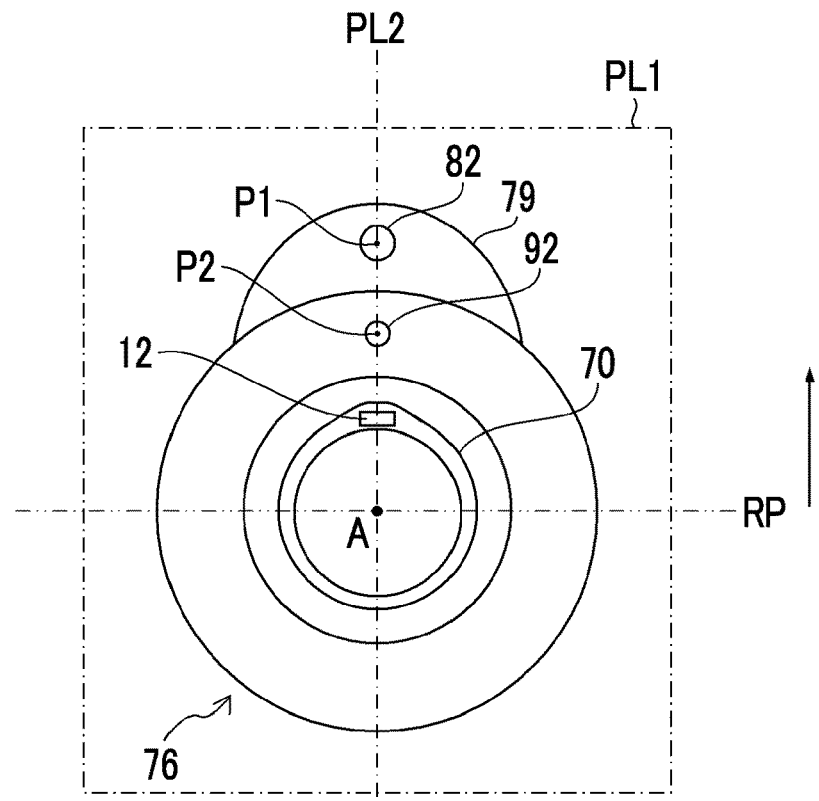
FIG. 5 is a view of the gripping cylinder viewed from a proximal end side along a center axis.

Next, a positional relationship between the first position P1 and the second position P2 will be described on the basis of FIG. 5. FIG. 5 is a view for explaining the relationship between the first position P1 and the second position P2 in the first configuration of the first embodiment. FIG. 5 is a view of the overtube 10 viewed from the proximal end side along the center axis A, in which the first connecting pipe 84 and the second connecting pipe 86 are removed. The first position P1 and the second position P2 are located on the proximal end side of the stopper 79 of the gripping cylinder 76. It should be noted that the first position P1 and the second position P2 are concepts for indicating a place. Therefore, the size, shape, and the like are not particularly limited, but FIG. 5 shows the first position P1 and the second position P2 including the sizes of the relay pipe line 82 and the liquid pipe line 92. Further, in FIG. 5, the air supply pipe line 12 is shown.

As shown in FIG. 5, in the first position P1 and the second position P2, in a case where the plane orthogonal to the center axis of the gripping cylinder 76 is defined as the first surface PL1, and the plane orthogonal to the first surface PL1 and intersecting the air supply pipe line 12 is defined as the second surface PL2, the first position P1 and the second position P2 are disposed on the same side with respect to a reference surface RP orthogonal to the first surface PL1 and orthogonal to the second surface PL2. The first position P1 and the second position P2 are disposed on the side of one outer peripheral surface of the gripping cylinder 76 with the reference surface RP as a boundary. Disposing the first position P1 and the second position P2 on the same side brings the first position P1 and the second position P2 closer to each other. In a case where the first position P1 and the second position P2 are brought close to each other, the first connecting pipe 84 extending outward from the first position P1 and the second connecting pipe 86 extending outward from the second position P2 are brought close to each other, and the operator easily grips the overtube 10.

In the first embodiment, the second surface PL2 intersecting the air supply pipe line 12 is applied to define the reference surface RP. The second surface PL2 makes it possible to determine the reference surface RP even in a case where the air supply pipe line 12 is not in a straight line along the axial direction of the center axis A of the gripping cylinder 76 or is formed in a slender shape in the circumferential direction of the gripping cylinder 76.

As shown in FIG. 5, it is preferable that the first position P1 and the second position P2 are at the same position in the circumferential direction of the center axis A of the gripping cylinder 76. In this configuration, the first position P1 and the second position P2 can be closest to each other in the circumferential direction. The same positions as each other mean that the first position P1 and the second position P2 are located on the same straight line in a case where a straight line is drawn from the center axis A in the outer peripheral direction. As shown in FIG. 5, the distance between the first position P1 and the second position P2 is different from the center axis A, so that the second position P2 and the first position P1 have an internal and external positional relationship in the radial direction with the center axis A as a reference.

Figure 6:
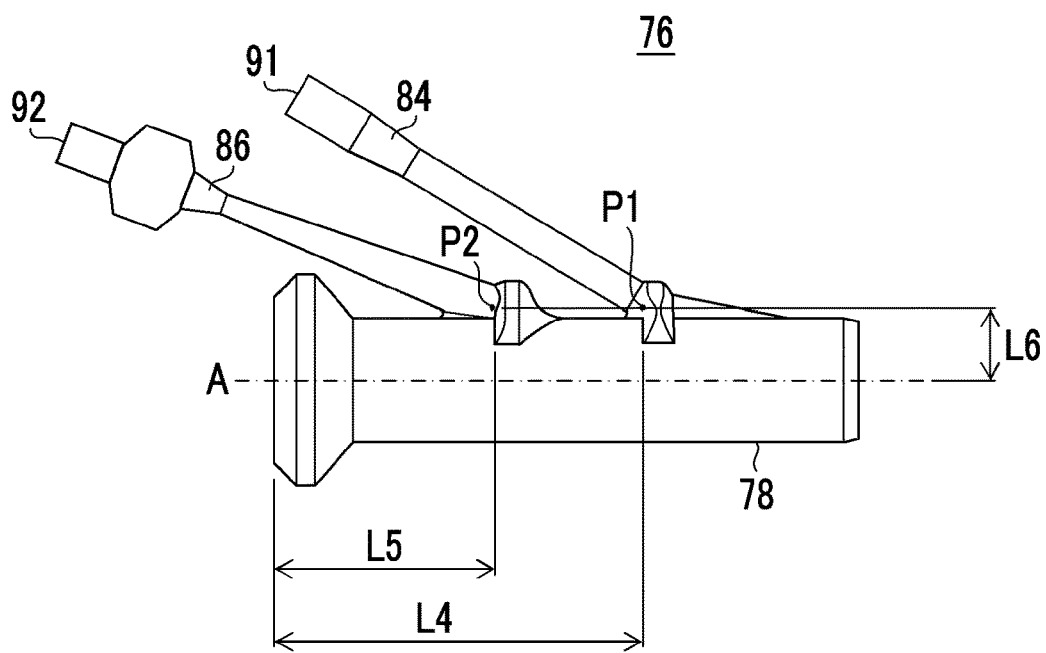
FIG. 6 is a side view of a gripping cylinder including the first connecting pipe and the second connecting pipe as viewed from the side of a gripping cylinder side portion.
Figure 7:
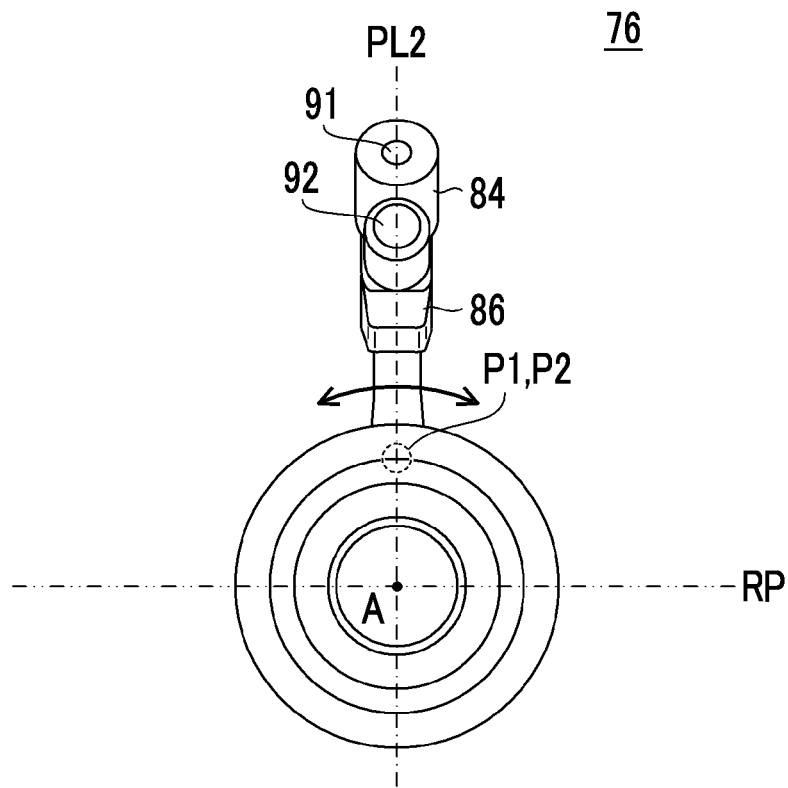
FIG. 7 is a view of the gripping cylinder of FIG. 6 viewed from a proximal end side along a center axis.

FIG. 6 and FIG. 7 are a view for explaining the relationship between the first position P1 and the second position P2 in the second configuration of the first embodiment. FIG. 6 is a side view of the gripping cylinder 76 including the first connecting pipe 84 and the second connecting pipe 86 from the side of the gripping cylinder side portion 78. FIG. 7 is a view of the gripping cylinder 76 of FIG. 6 viewed from the proximal end side along the center axis A.

At the first position P1 and the second position P2 shown in FIG. 6, the distance L4 to the first position P1 is longer than the distance L5 to the second position P2 with the proximal end of the gripping cylinder 76 as a reference. With the center axis A as a reference, the distance L6 from the center axis A is equal. The first position P1 and the second position P2 are disposed in parallel along the length direction of the center axis A.

As shown in FIG. 7, even in a case where the first position P1 and the second position P2 are disposed in parallel along the center axis A, the first position P1 and the second position P2 are disposed on the same side with respect to the reference surface RP. Similar to the first configuration, in a case where the plane orthogonal to the center axis A of the gripping cylinder 76 is defined as the first surface PL1 (not shown), and the plane orthogonal to the first surface and intersecting the air supply pipe line 12 is defined as the second surface PL2, the reference surface RP is a plane orthogonal to the first surface PL1 and orthogonal to the second surface PL2.

In addition, as shown in FIG. 7, it is preferable that the first position P1 and the second position P2 are at the same position in the circumferential direction (direction indicated by the arrow) of the center axis A of the gripping cylinder 76. In this configuration, the first position P1 and the second position P2 can be closest to each other in the circumferential direction. Since the distance between the first position P1 and the second position P2 is different from the proximal end of the gripping cylinder 76, the first position P1 and the second position P2 have a positional relationship of perspective with the proximal end as a reference (refer to FIG. 6).

Figure 8:
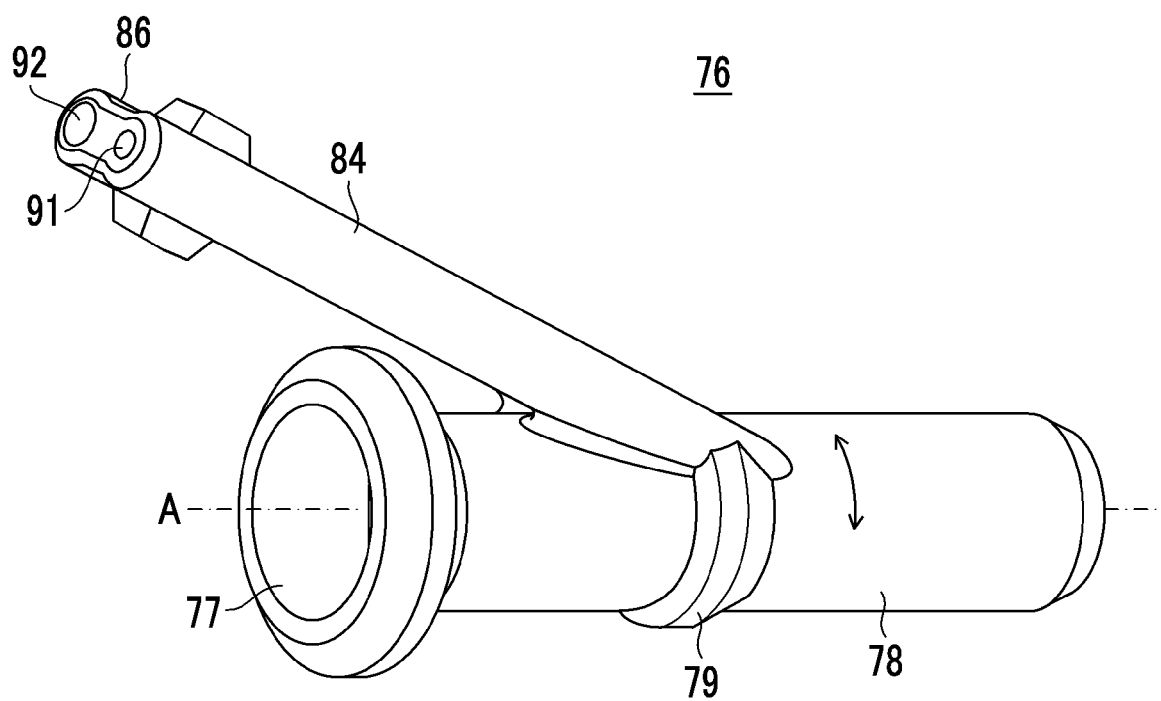
FIG. 8 is a perspective view of a gripping cylinder including the first connecting pipe and the second connecting pipe as viewed from a proximal end side of a gripping cylinder.
Figure 9:
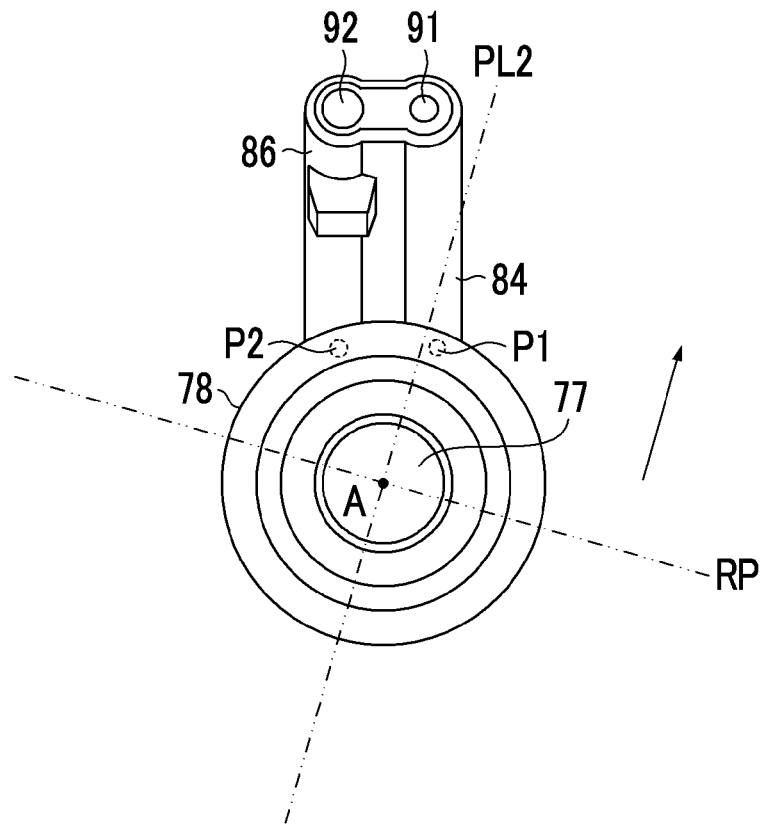
FIG. 9 is a view of the gripping cylinder of FIG. 8 viewed from a proximal end side along a center axis.

Other aspects of the positional relationship between the first position P1 and the second position P2 will be described. FIG. 8 and FIG. 9 are a view for explaining the positional relationship between the first position P1 and the second position P2 in the third configuration of the first embodiment. FIG. 8 is a perspective view of a gripping cylinder 76 including the first connecting pipe 84 and the second connecting pipe 86 as viewed from a proximal end side of a gripping cylinder 76. FIG. 9 is a view of the gripping cylinder 76 of FIG. 8 viewed from the proximal end side along the center axis A.

As shown in FIG. 8, the gripping cylinder 76 comprises the first connecting pipe 84 extending outward from the first position P1, the second connecting pipe 86 extending outward from the second position P2, and the stopper 79. The stopper 79 is continuously provided over the entire outer circumference of the gripping cylinder side portion 78.

As shown in FIG. 8, the first connecting pipe 84 and the second connecting pipe 86 are disposed in parallel in the circumferential direction of the gripping cylinder 76 as shown by the arrow. As shown in FIG. 8 and FIG. 9, the first connecting pipe 84 and the second connecting pipe 86 are formed as an inseparable integrally molded body. In the third aspect, there is no gap between the first connecting pipe 84 and the second connecting pipe 86.

As shown in FIG. 9, in the third configuration, as in the first configuration and the second configuration, the first position P1 and the second position P2 are disposed on the same side with respect to the reference surface RP. The operator can easily grip the gripping cylinder 76.

Figure 10:
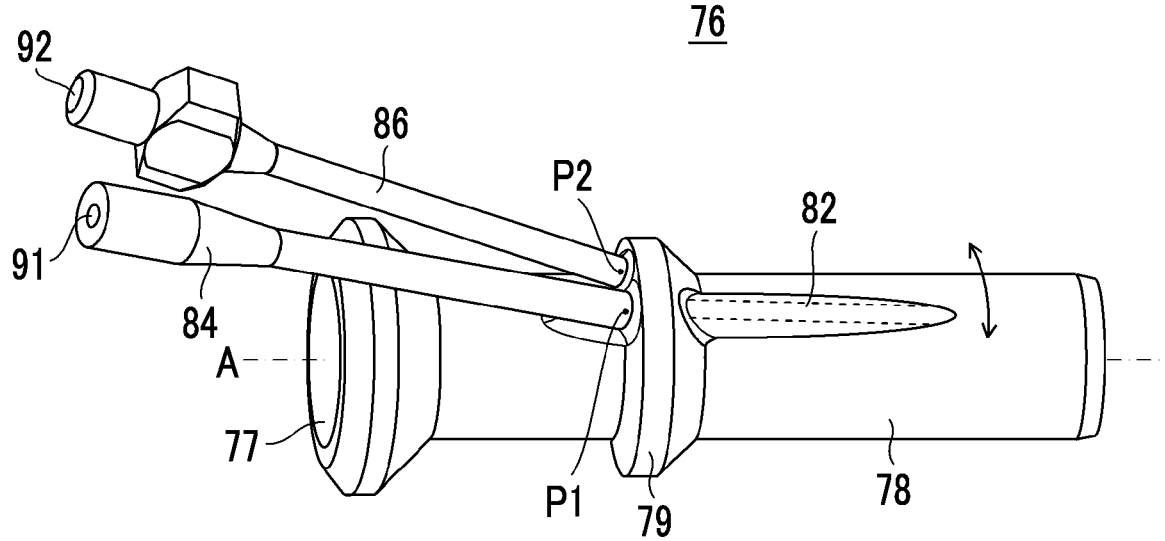
FIG. 10 is a perspective view of a gripping cylinder including the first connecting pipe and the second connecting pipe.
Figure 11:
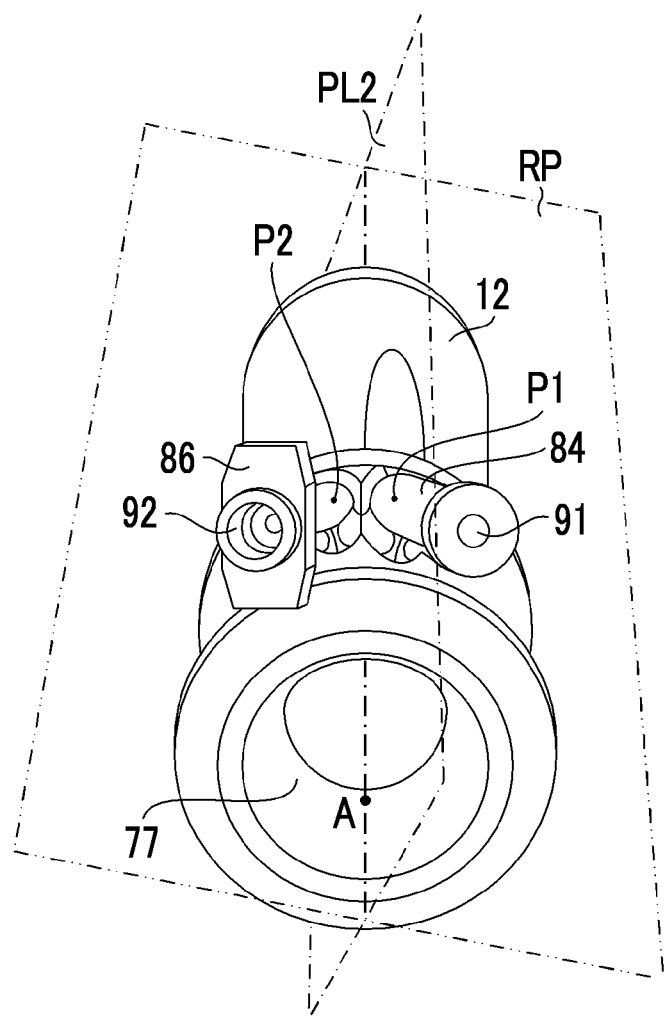
FIG. 11 is a perspective view of the gripping cylinder of FIG. 10 as viewed from the proximal end side.

FIG. 10 and FIG. 11 are a view for explaining the positional relationship between the first position P1 and the second position P2 in the fourth configuration of the first embodiment. FIG. 10 is a perspective view of a gripping cylinder 76 including the first connecting pipe 84 and the second connecting pipe 86. FIG. 11 is a perspective view of the gripping cylinder 76 of FIG. 10 as viewed from the proximal end side.

As shown in FIG. 10, the gripping cylinder 76 comprises the first connecting pipe 84 extending outward from the first position P1, the second connecting pipe 86 extending outward from the second position P2, and the stopper 79. The stopper 79 is continuously provided over the entire outer circumference of the gripping cylinder side portion 78. As shown in FIG. 11, the first position P1 and the second position P2 are disposed in parallel in the circumferential direction of the center axis A as shown by the arrow.

As shown in FIG. 10 and FIG. 11, the fourth configuration is different from the third configuration, and the first connecting pipe 84 and the second connecting pipe 86 are individually formed. In the fourth configuration, as in the first configuration and the second configuration, there is a gap between the first connecting pipe 84 and the second connecting pipe 86.

As shown in FIG. 11, in the fourth configuration, the first position P1 and the second position P2 are disposed on the same side with respect to the reference surface RP, as in the first to third configurations. The operator can easily grip the gripping cylinder 76.

Next, a preferred embodiment of the first embodiment will be described. As shown in FIG. 3, an angle θ1 of the pipe line axis 91A of the gas pipe line 91 in which the first connecting pipe 84 is formed with respect to the reference surface RP is preferably 40 degrees or less.

As described above, the gripping cylinder 76 is the integrally molded body in which the first connecting pipe 84 and the second connecting pipe 86 are integrally molded. The integral molding is performed using, for example, two molds having a cavity (internal space). The integral molding step includes steps of (1) clamping the 2 molds and forming a cavity in the mold having the shape of the gripping cylinder 76 (internal space), (2) filling the cavity with molten resin, (3) solidifying the resin, and (4) releasing the mold from the integrally molded body.

By setting the angle θ1 of the pipe line axis 91A of the gas pipe line 91 to 40 degrees or less, the mold can be easily released from the integrally molded body, and the gas pipe line 91 can be easily molded. Since the mold is easily released by setting the angle θ1 to 40 degrees or less, the damage resistance of the gripping cylinder 76, which is an integrally molded body, can be improved.

As shown in FIG. 3, in a case where the distance between the center axis A of the gripping cylinder 76 and the first position P1 is defined as the first distance L1, and the distance between the center axis A of the gripping cylinder 76 and the second position P2 is defined as the second distance L2, it is preferable that the first distance L1 is larger than the second distance L2.

Making the first distance L1 larger than the second distance L2 makes it possible to extend the air supply pipe line 12 from the gripping cylinder 76 to the second balloon BL2 of the tube main body 70. In a case where the second distance L2 is larger than the first distance L1, there is a concern that the liquid pipe line 83 inside the gripping cylinder 76 may prevent the air supply pipe line 12 from extending to the second balloon BL2.

Having the first position P1 and the second position P2 in the above-described positional relationship makes it possible to dispose the second connecting pipe 86 between the first connecting pipe 84 and the gripping cylinder 76.

In addition, in the gas pipe line 91 of the first connecting pipe 84 and the liquid pipe line 92 of the second connecting pipe 86 of the gripping cylinder 76, the gas pipe line 91 is preferably disposed at a position outside the liquid pipe line 92 with respect to the center axis A.

Since the gas pipe line 91 of the gripping cylinder 76 is located outside the liquid pipe line 92 with respect to the center axis A, in a case where the gripping cylinder 76 is gripped by the operator, the tube 106 from the apparatus for supplying air into the second balloon BL2 can be located at a position where it is difficult to be obstructed.

The position outside the center axis A means that the distance from the center axis A is longer in the gas pipe line 91 than in the liquid pipe line 92.

Figure 12:
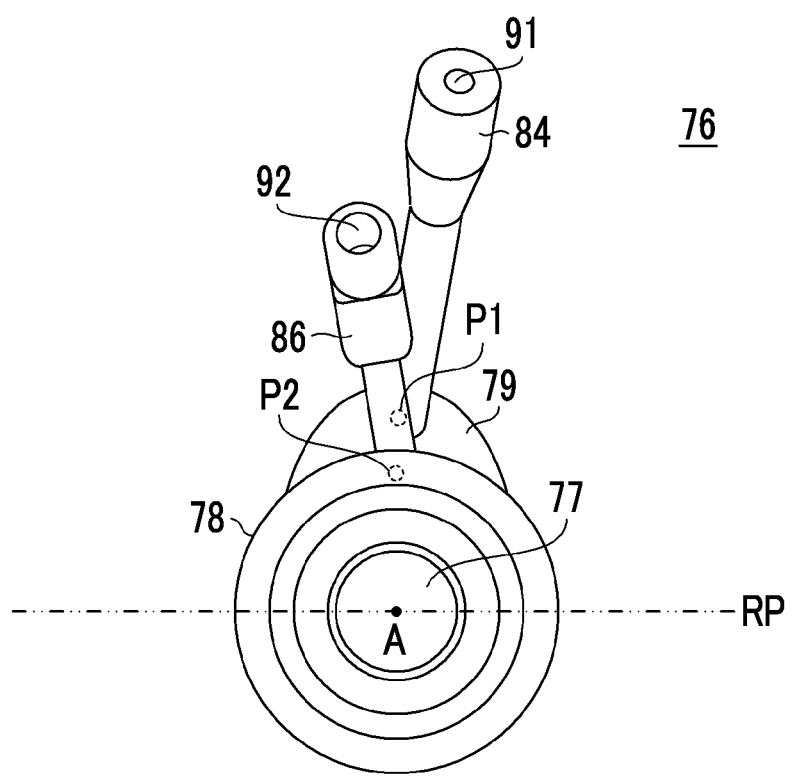
FIG. 12 is a view of the gripping cylinder viewed from a proximal end side along a center axis.

FIG. 12 is a view of the gripping cylinder 76 viewed from the proximal end side along the center axis A. As shown in FIG. 12, in a case where the first connecting pipe 84 and the second connecting pipe 86 are projected on the plane (not shown) orthogonal to the center axis A of the gripping cylinder 76, it is preferable that at least a part of the regions of the first connecting pipe 84 or the second connecting pipe 86 overlap each other.

The first connecting pipe 84 and the second connecting pipe 86 have physical sizes (here, the size of the first connecting pipe 84 and the second connecting pipe 86 in the diameter direction) different from the first position P1 and the second position P2. The first connecting pipe 84 and the second connecting pipe 86 having the physical size can overlap each other in at least a part of the region. This overlap makes it possible to bring the first connecting pipe 84 and the second connecting pipe 86 closer to each other, and the gripping cylinder 76 can be miniaturized. The size of the overlapping region of the first connecting pipe 84 and the second connecting pipe 86 can be changed by the size of the diameters of the first connecting pipe 84 and the second connecting pipe 86.

Figure 13:
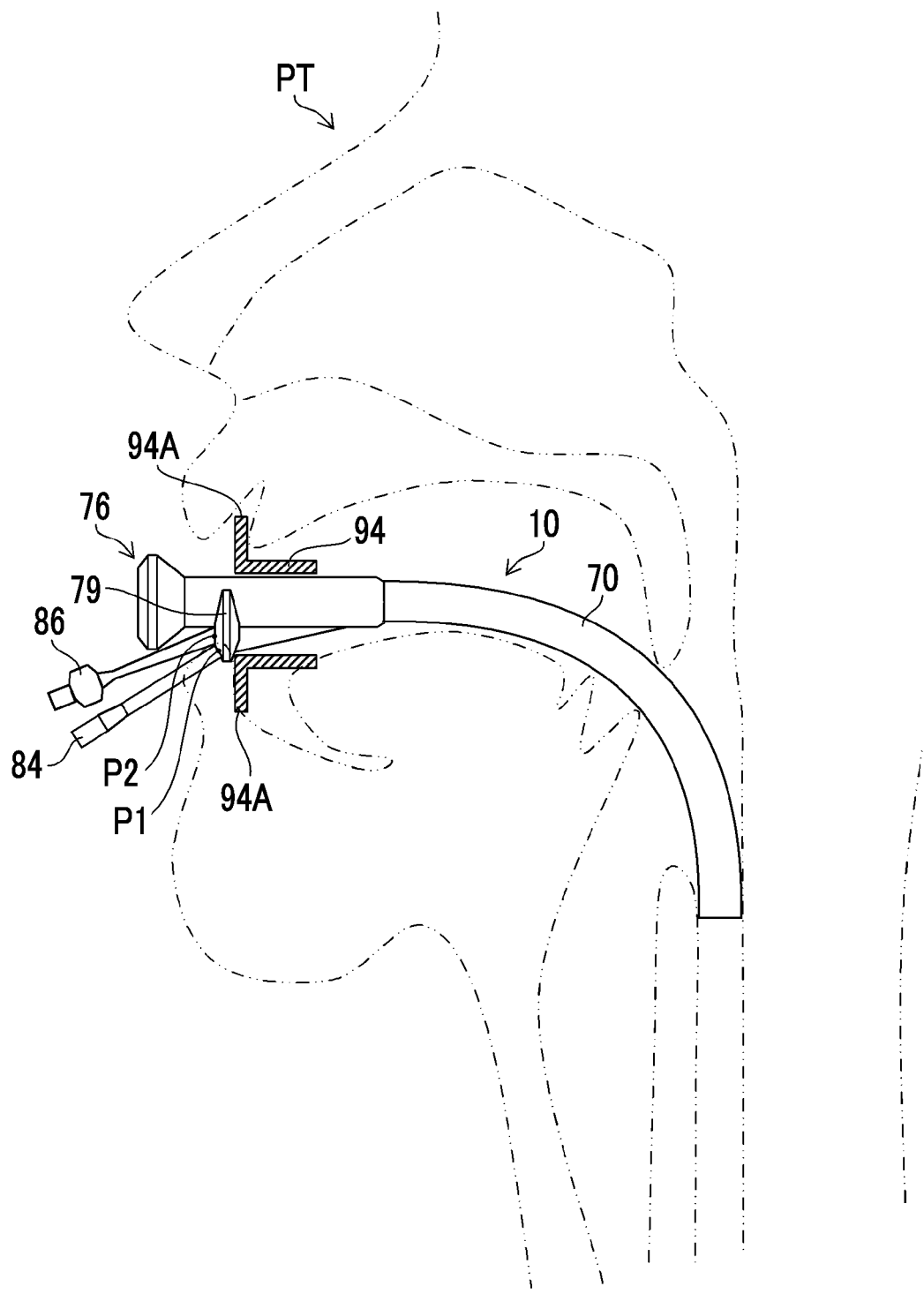
FIG. 13 is a view showing a state in which an overtube is mounted to a subject.

FIG. 13 is a view showing a state in which the overtube 10 is orally mounted to a subject PT. As shown in FIG. 13, the subject PT holds a mouthpiece 94 in his mouth.

The mouthpiece 94 is a member that the subject PT holds in the mouth, and is formed in a tubular shape by resin. A flange 94A is formed on one opening side of the mouthpiece 94. The flange 94A prevents the subject PT from swallowing the mouthpiece 94.

The insertion part 18 (not shown) of the endoscope 14 is inserted into the endoscope insertion passage 11 of the overtube 10. The overtube 10 is mounted to the proximal end side of the insertion part 18. The endoscope 14 mounted with the overtube 10 is inserted into the body cavity of the subject PT from the oral cavity via the mouthpiece 94.

The stopper 79 of the gripping cylinder 76 of the overtube 10 is in contact with the flange 94A of the mouthpiece 94. The contact between the stopper 79 and the mouthpiece 94 fixes the position of the overtube 10 with respect to the subject PT, and determines the length of the overtube 10 inserted into the body cavity of the subject PT. The distal end side from the first position P1 and the second position P2 of the overtube 10 is inserted into the body cavity of the subject PT.

FIG. 13 exemplifies the gripping cylinder 76 comprising the stopper 79. In a case where the gripping cylinder 76 does not have the stopper 79, one of the first connecting pipe 84 extending from the first position P1 or the second connecting pipe 86 extending from the second position P2 is in contact with the flange 94A of the mouthpiece 94. The contact between the first connecting pipe 84 or the second connecting pipe 86 and the mouthpiece 94 fixes the position of the overtube 10 with respect to the subject PT, and determines the length of the overtube 10 inserted into the body cavity of the subject PT.

As shown in FIG. 13, the first position P1 and the second position P2 are preferably disposed at positions closer to the proximal end of the gripping cylinder 76 than the distal end of the gripping cylinder 76. Disposing the first position P1 and the second position P2 on the proximal end side of the gripping cylinder 76 can increase the length of the overtube 10 that can be inserted into the body cavity of the subject PT.

Second Embodiment

An overtube of the second embodiment will be described. The same configuration as those in the first embodiment may be designated by the same reference numerals and the description thereof may be omitted. The second embodiment has the same basic configuration as the first embodiment, but specifies the invention from another viewpoint. That is, the first position and the second position can be determined regardless of the position of the air supply pipe line.

Figure 14:
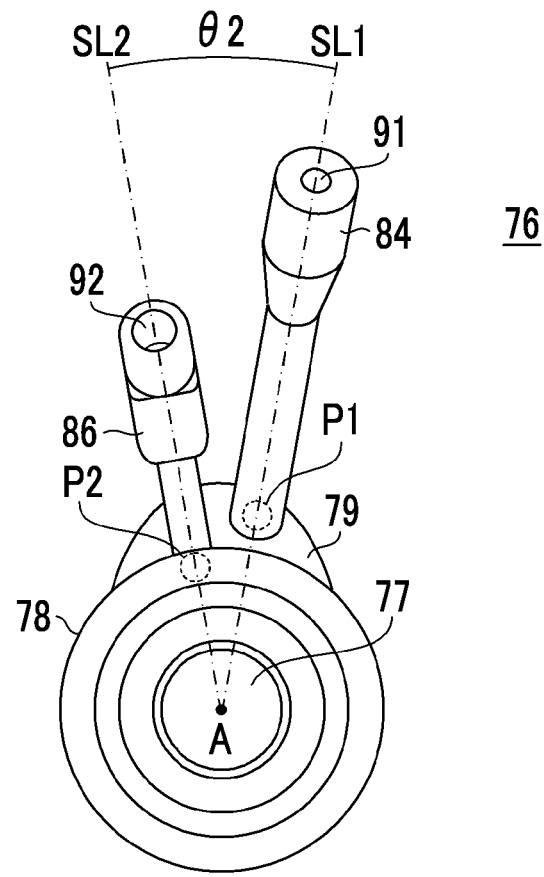
FIG. 14 is a view of the gripping cylinder viewed from a proximal end side along a center axis.

FIG. 14 is a view of the gripping cylinder 76 viewed from the proximal end side along the center axis A. As shown in FIG. 14, the gripping cylinder 76 comprises the first connecting pipe 84 extending from the first position P1 of the gripping cylinder side portion 78 to the proximal end side, the second connecting pipe 86 extending from the second position P2 of the gripping cylinder side portion 78 to the proximal end side, and the second insertion passage 77. The gripping cylinder 76 is an integrally molded body in which the first connecting pipe 84 and the second connecting pipe 86 are integrally molded.

The gripping cylinder side portion 78 of the gripping cylinder 76 preferably has a flange-shaped stopper 79 formed to extend outward from the inside in the radial direction of the center axis A of the gripping cylinder 76. The first position P1 and the second position P2 are located on the surface of the stopper 79 on the proximal end side.

In the gripping cylinder 76 of the second embodiment, as viewed from the axial direction of the center axis A of the gripping cylinder 76, an angle $\theta 2$ formed by the first straight line SL1 connecting the center axis A and the first position P1 and the second straight line SL2 connecting the center axis A and the second position P2 is an acute angle or 0 degrees. Setting the angle $\theta 2$ to an acute angle or 0 degrees makes it possible to dispose the first position P1 and the second position P2 close to each other. The positional relationship between the first position P1 and the second position P2 makes it possible to dispose the first connecting pipe 84 and the second connecting pipe 86 so as to be close to the circumferential direction of the center axis A. The operator can easily grip the gripping cylinder 76. The angle $\theta 2$ formed by the first straight line SL1 and the second straight line SL2 is the smaller of the two angles defined by the first straight line SL1 and the second straight line SL2. In the second embodiment, the first position P1 and the second position P2 can be determined without being affected by the position of the air supply pipe line 12 (not shown) of the overtube 10.

In the second embodiment, the case where the first position P1 and the second position P2 are juxtaposed in the circumferential direction of the center axis A is exemplified. The arrangement of the first position P1 and the second position P2 is not limited to this, and the distance from the proximal end of the gripping cylinder 76 to the first position P1 and the distance from the proximal end to the second position P2 may be different. In this case, as viewed from the axial direction of the center axis A of the gripping cylinder 76, an angle $\theta 2$ formed by the first straight line SL1 connecting the center axis A and the first position P1 and the second straight line SL2 connecting the center axis A and the second position P2 may be an acute angle or 0 degrees.

In the second embodiment, the same preferred configurations and embodiments as in the first embodiment can be applied without departing from the scope of the invention.

Third Embodiment

An overtube of the third embodiment will be described. The same configuration as those in the first embodiment and the second embodiment may be designated by the same reference numerals and the description thereof may be omitted. In the third embodiment, as compared with the first embodiment and the second embodiment, the gripping cylinder of the overtube comprises the stopper, and the first position and the second position are disposed at the position on the stopper or between the proximal end and the stopper. Regardless of the first position and second position, the stopper determines the length of the overtube inserted into the body cavity of the subject.

Figure 15:
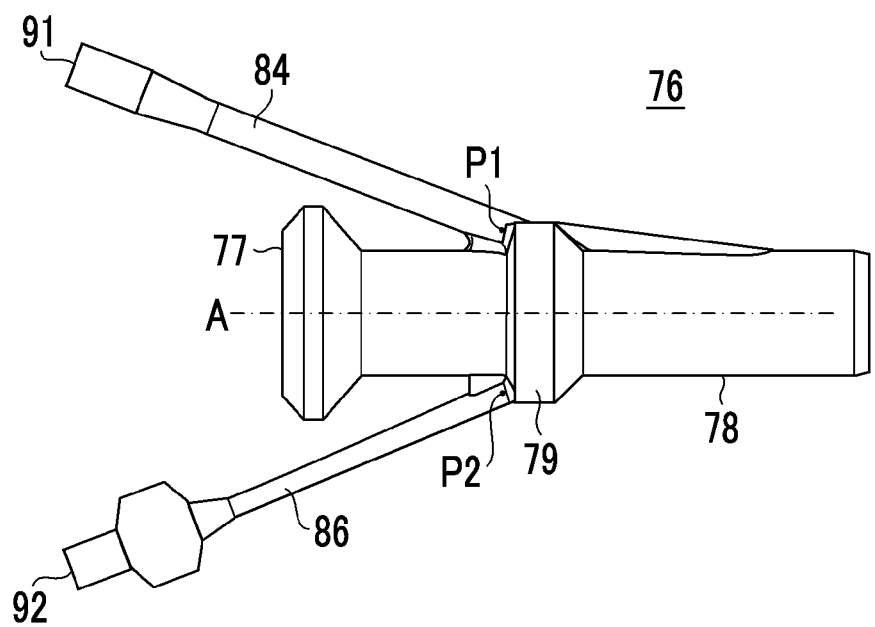
FIG. 15 is a side view of a gripping cylinder including the first connecting pipe and the second connecting pipe as viewed from the side of a gripping cylinder side portion.
Figure 16:
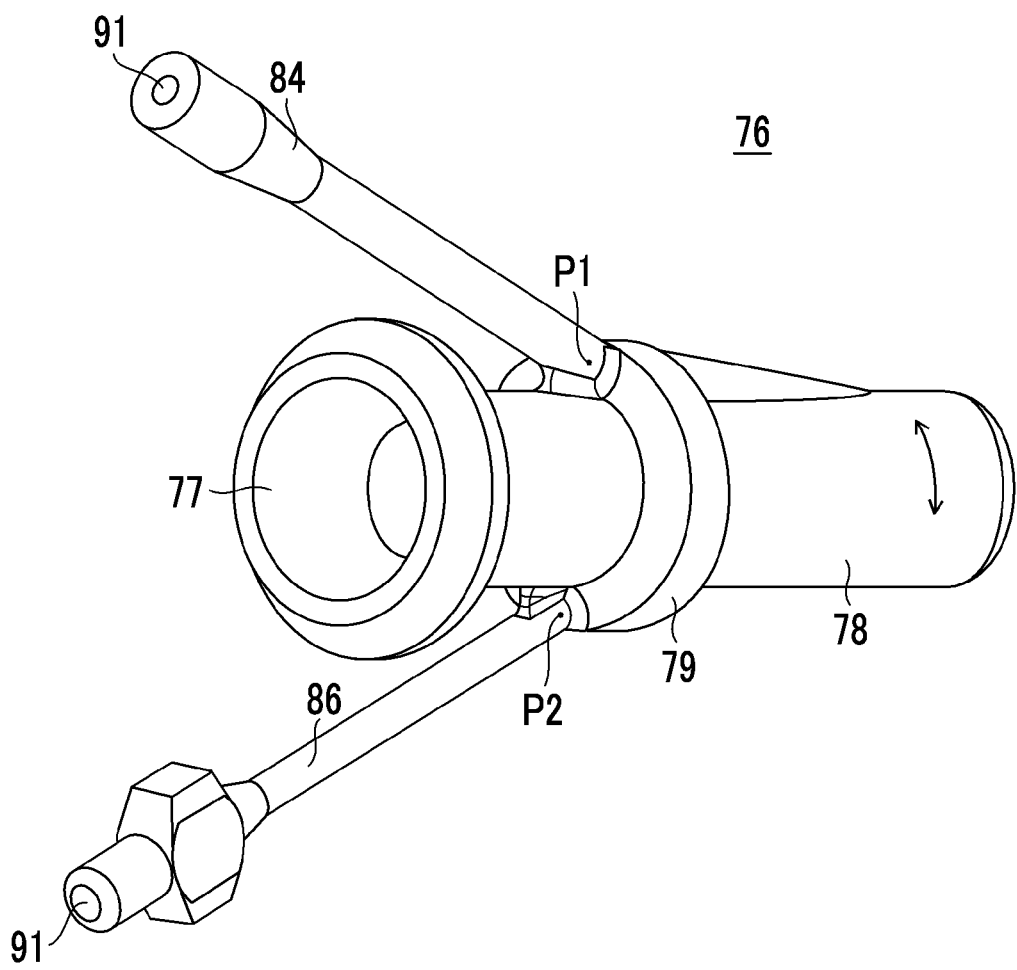
FIG. 16 is a perspective view of a gripping cylinder including the first connecting pipe and the second connecting pipe as viewed from a proximal end side of a gripping cylinder.

FIG. 15 is a side view of the gripping cylinder 76 including the first connecting pipe 84 and the second connecting pipe 86 as viewed from the side of the gripping cylinder side portion 78. FIG. 16 is a perspective view of a gripping cylinder including the first connecting pipe 84 and the second connecting pipe 86 as viewed from a proximal end side of a gripping cylinder 76.

As shown in FIG. 15 and FIG. 16, the gripping cylinder 76 comprises the first connecting pipe 84 extending from the first position P1 of the gripping cylinder side portion 78 to the proximal end side, the second connecting pipe 86 extending from the second position P2 of the gripping cylinder side portion 78 to the proximal end side, and the second insertion passage 77. The gripping cylinder 76 is an integrally molded body in which the first connecting pipe 84 and the second connecting pipe 86 are integrally molded.

Figure 17:
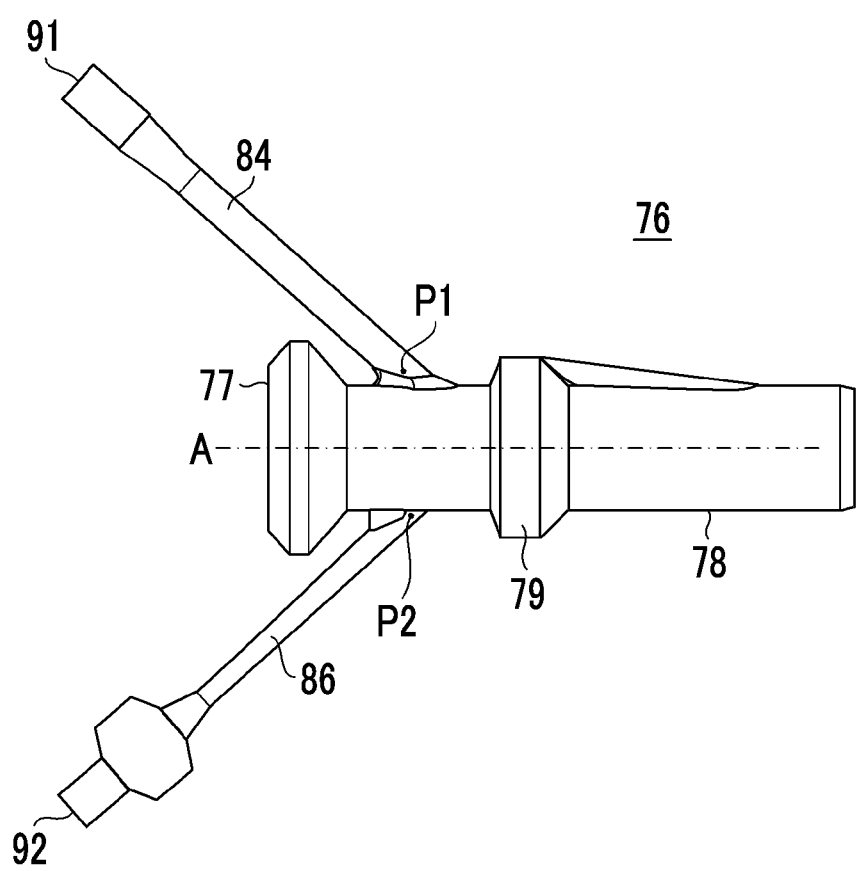
FIG. 17 is a side view of a gripping cylinder including the first connecting pipe and the second connecting pipe as viewed from the side of a gripping cylinder side portion.

The gripping cylinder side portion 78 of the gripping cylinder 76 has a flange-shaped stopper 79 formed to extend outward from the inside in the radial direction of the center axis of the gripping cylinder 76. The first position P1 and the second position P2 are formed on the stopper 79. In FIG. 15 and FIG. 16, the case where the first position P1 and the second position P2 are formed on the stopper 79 is exemplified. However, the structure is not limited to this, and as shown in FIG. 17, the first position P1 and the second position P2 can be positioned between the proximal end of the gripping cylinder 76 and the stopper 79.

Figure 18:
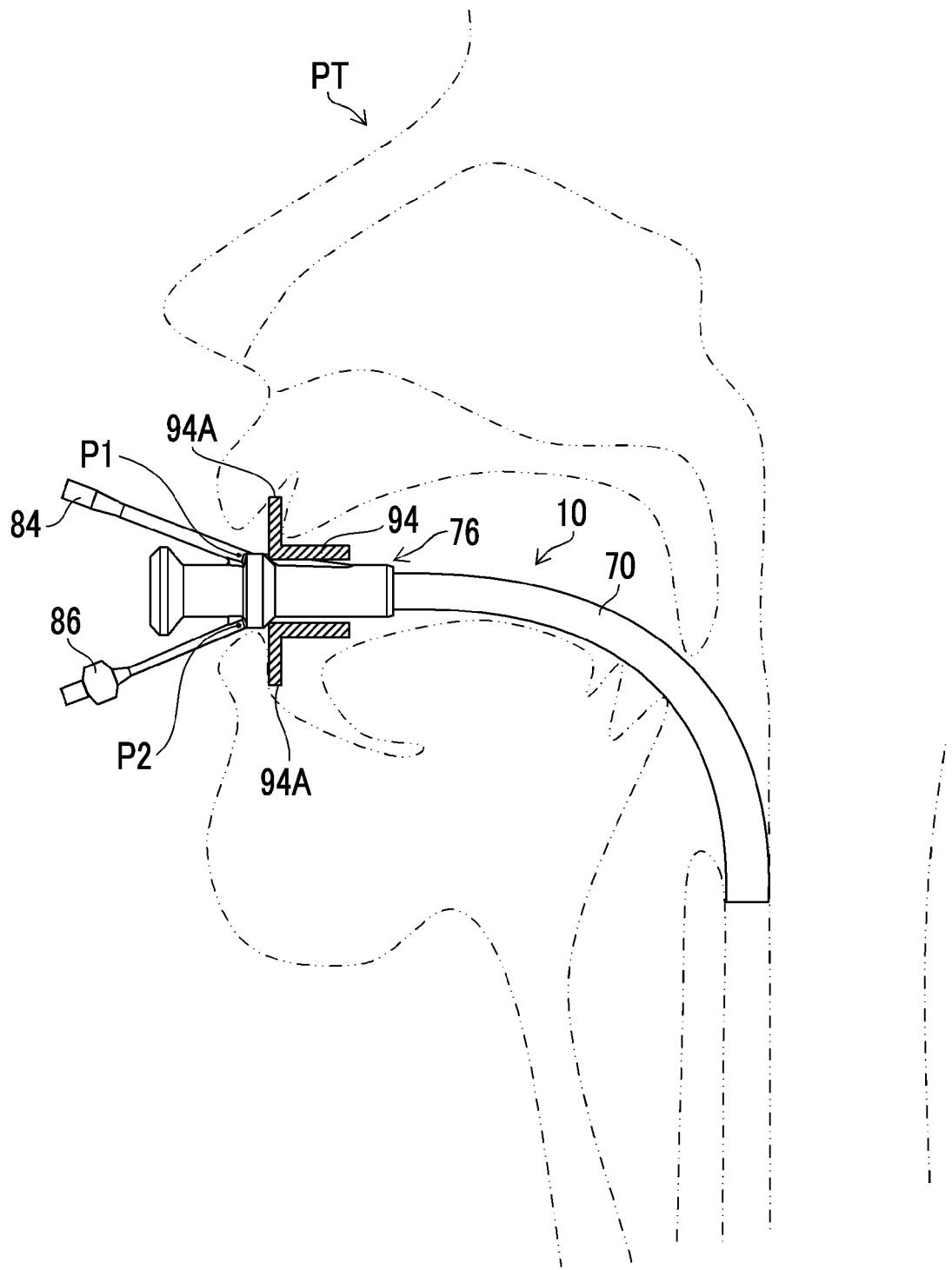
FIG. 18 is a view showing a state in which an overtube of the third embodiment is mounted to a subject.

FIG. 18 is a view showing a state in which the overtube 10 of the third embodiment is orally mounted to the subject PT. As shown in FIG. 18, the subject PT holds a mouthpiece 94 in his mouth.

The insertion part 18 (not shown) of the endoscope 14 is inserted into the endoscope insertion passage 11 of the overtube 10. The overtube 10 is mounted to the proximal end side of the insertion part 18. The endoscope 14 mounted with the overtube 10 is inserted into the body cavity of the subject PT from the oral cavity via the mouthpiece 94.

The stopper 79 of the gripping cylinder 76 of the overtube 10 is in contact with the flange 94A of the mouthpiece 94. The contact between the stopper 79 and the mouthpiece 94 fixes the position of the overtube 10 with respect to the subject PT, and determines the length of the overtube 10 inserted into the body cavity of the subject PT.

The position of the overtube 10 is fixed by the stopper 79, and the length of the overtube 10 that can be inserted into the body cavity of the subject PT can be increased. The stopper 79 is preferably provided at the position closer to the proximal end than the distal end of the gripping cylinder 76.

Also in the third embodiment, the same preferred embodiments as those in the first embodiment and the second embodiment can be applied without departing from the scope of the invention.

EXPLANATION OF REFERENCES

1: endoscope apparatus
10: overtube
11: endoscope insertion passage
12: air supply pipe line
14: endoscope
16: hand operation portion
18: insertion part
20: universal cable
21A: connector
21B: connector
24: light source apparatus
30: processor
32: air supply and water supply button
34: suction button
36: shutter button
38: angle knob
39: treatment tool insertion part
42: balloon air supply port
44: flexible portion
46: curved portion
48: distal end portion
50: distal end surface
52: observation window
54: illumination window
56: air supply and water supply nozzle
58: forceps port
60: monitor
70: tube main body
70A: pipe line
71: first insertion passage
76: gripping cylinder
76A: pipe line
77: second insertion passage
78: gripping cylinder side portion
79: stopper
82: relay pipe line
84: first connecting pipe
86: second connecting pipe
91: gas pipe line
91A: pipe line axis
92: liquid pipe line
94: mouthpiece
94A: flange
100: balloon control apparatus
104: tube
106: tube
A: center axis
BL1: first balloon
BL2: second balloon
L1, L2, L3, L4, L5, L6: distance
LP1: first distance
LP2: second distance
P1: first position
P2: second position
PL1: first surface
PL2: second surface
PT: subject
RP: reference surface
SL1: first straight line
SL2: second straight line
θ1, θ2: angle

What is claimed is:

1. An overtube having an endoscope insertion passage through which an endoscope can be inserted, the overtube comprising:
a tube main body in which a first insertion passage constituting a part of the endoscope insertion passage is formed;
a gripping cylinder that is connected to a proximal end side of the tube main body, in which a second insertion passage constituting another part of the endoscope insertion passage is formed;
a balloon that is mounted to an outer peripheral surface on a distal end side of the tube main body; and
an air supply pipe line that is arranged to be parallel to the endoscope insertion passage from the tube main body to the gripping cylinder and communicates with the balloon, wherein the tube main body has a third insertion passage separated from the first insertion passage by an inner peripheral surface of the tube main body, and a portion of the air supply pipe line is formed inside the third insertion passage and between an outer peripheral surface and the inner peripheral surface of the tube main body, wherein
the gripping cylinder includes
a first connecting pipe that extends obliquely outward from a first position of a gripping cylinder side portion between a proximal end and a distal end of the gripping cylinder toward the proximal end side of the gripping cylinder, and has a gas pipe line communicating with the air supply pipe line; and
a second connecting pipe that extends obliquely outward from a second position different from the first position of the gripping cylinder side portion toward the proximal end side of the gripping cylinder and has a liquid pipe line communicating with the second insertion passage,
the gripping cylinder is an integrally molded body in which the first connecting pipe and the second connecting pipe are integrally molded, and
in a case where a plane orthogonal to a center axis of the gripping cylinder is defined as a first surface, and a plane orthogonal to the first surface and intersecting the air supply pipe line is defined as a second surface, the first position and the second position are disposed on the same side with respect to a reference surface orthogonal to the first surface and orthogonal to the second surface,
wherein an angle of a pipe line axis of the gas pipe line with respect to the reference surface is different from an angle of a pipe line axis of the liquid pipe line with respect to the reference surface.

2. The overtube according to claim 1, wherein
the gripping cylinder side portion has a flange-shaped stopper formed to extend outward from an inside in a radial direction of the center axis of the gripping cylinder, and
the first position and the second position are positioned on a surface of the proximal end side of the stopper.

3. The overtube according to claim 1, wherein
the gripping cylinder side portion has a relay pipe line that forms a part of the air supply pipe line and communicates with the gas pipe line, and
the gas pipe line and the relay pipe line are bent and connected.

4. The overtube according to claim 3, wherein
the gas pipe line is provided so as to be inclined obliquely outward toward the proximal end side of the gripping cylinder from the relay pipe line.

5. The overtube according to claim 4, wherein
the angle of the pipe line axis of the gas pipe line with respect to the reference surface is 40 degrees or less.

6. The overtube according to claim 1, wherein
in a case where the first connecting pipe and the second connecting pipe are projected on the plane orthogonal to the center axis of the gripping cylinder, regions of at least parts of the first connecting pipe and the second connecting pipe overlap each other.

7. The overtube according to claim 1, wherein
the first position and the second position are at the same position in a circumferential direction of the center axis of the gripping cylinder.

8. The overtube according to claim 1, wherein
in a case where a distance between the center axis of the gripping cylinder and the first position is defined as a first distance and a distance between the center axis of the gripping cylinder and the second position is defined as a second distance, the first distance is larger than the second distance.

9. The overtube according to claim 1, wherein
the second connecting pipe is provided between the first connecting pipe and the gripping cylinder.

10. The overtube according to claim 1, wherein
the first position and the second position are positions closer to the proximal end of the gripping cylinder than the distal end of the gripping cylinder.

11. The overtube according to claim 1, wherein
in the gas pipe line and the liquid pipe line of the gripping cylinder, the gas pipe line is disposed at a position outside the liquid pipe line with respect to the center axis of the gripping cylinder.

12. An overtube having an endoscope insertion passage through which an endoscope can be inserted, the overtube comprising:
a tube main body in which a first insertion passage constituting a part of the endoscope insertion passage is formed;
a gripping cylinder that is connected to a proximal end side of the tube main body, in which a second insertion passage constituting another part of the endoscope insertion passage is formed;
a balloon that is mounted to an outer peripheral surface on a distal end side of the tube main body; and
an air supply pipe line that is arranged to be parallel to the endoscope insertion passage from the tube main body to the gripping cylinder and communicates with the balloon, wherein the tube main body has a third insertion passage separated from the first insertion passage by an inner peripheral surface of the tube main body, and a portion of the air supply pipe line is formed inside the third insertion passage and between an outer peripheral surface and the inner peripheral surface of the tube main body, wherein
the gripping cylinder includes
    a first connecting pipe that extends obliquely outward from a first position of a gripping cylinder side portion between a proximal end and a distal end of the gripping cylinder toward the proximal end side of the gripping cylinder, and has a gas pipe line communicating with the air supply pipe line; and
    a second connecting pipe that extends obliquely outward from a second position different from the first position of the gripping cylinder side portion toward the proximal end of the gripping cylinder and has a liquid pipe line communicating with the second insertion passage,
the gripping cylinder is an integrally molded body in which the first connecting pipe and the second connecting pipe are integrally molded, and
as viewed from an axial direction of a center axis of the gripping cylinder, an angle formed by a first straight line connecting the center axis and the first position and a second straight line connecting the center axis and the second position is an acute angle or 0 degrees, wherein
in a case where a plane orthogonal to the center axis of the gripping cylinder is defined as a first surface, and a plane orthogonal to the first surface and intersecting the air supply pipe line is defined as a second surface, the first position and the second position are disposed on the same side with respect to a reference surface orthogonal to the first surface and orthogonal to the second surface,
wherein an angle of a pipe line axis of the gas pipe line with respect to the reference surface is different from an angle of a pipe line axis of the liquid pipe line with respect to the reference surface.

13. The overtube according to claim 12, wherein
the gripping cylinder side portion has a flange-shaped stopper formed to extend outward from an inside in a radial direction of the center axis of the gripping cylinder, and
the first position and the second position are positioned on a surface of the proximal end side of the stopper.

14. The overtube according to claim 12, wherein
the gripping cylinder side portion has a relay pipe line that forms a part of the air supply pipe line and communicates with the gas pipeline, and
the gas pipe line and the relay pipe line are bent and connected.

15. The overtube according to claim 12, wherein
in a case where the first connecting pipe and the second connecting pipe are projected on the plane orthogonal to the center axis of the gripping cylinder, regions of at least parts of the first connecting pipe and the second connecting pipe overlap each other.

16. The overtube according to claim 12, wherein
the first position and the second position are at the same position in a circumferential direction of the center axis of the gripping cylinder.

17. The overtube according to claim 12, wherein
in a case where a distance between the center axis of the gripping cylinder and the first position is defined as a first distance and a distance between the center axis of the gripping cylinder and the second position is defined as a second distance, the first distance is larger than the second distance.

18. The overtube according to claim 12, wherein
the second connecting pipe is provided between the first connecting pipe and the gripping cylinder.

19. An overtube having an endoscope insertion passage through which an endoscope can be inserted, the overtube comprising:
- a tube main body in which a first insertion passage constituting a part of the endoscope insertion passage is formed;
- a gripping cylinder that is connected to a proximal end side of the tube main body, in which a second insertion passage constituting another part of the endoscope insertion passage is formed;
- a balloon that is mounted to an outer peripheral surface on a distal end side of the tube main body; and
- an air supply pipe line that is arranged to be parallel to the endoscope insertion passage from the tube main body to the gripping cylinder and communicates with the balloon, wherein the tube main body has a third insertion passage separated from the first insertion passage by an inner peripheral surface of the tube main body, and a portion of the air supply pipe line is formed inside the third insertion passage and between an outer peripheral surface and the inner peripheral surface of the tube main body, wherein the gripping cylinder includes
- a first connecting pipe that extends obliquely outward from a first position of a gripping cylinder side portion between a proximal end and a distal end of the gripping cylinder toward the proximal end side of the gripping cylinder, and has a gas pipe line communicating with the air supply pipe line; and
- a second connecting pipe that extends obliquely outward from a second position different from the first position of the gripping cylinder side portion toward the proximal end of the gripping cylinder and has a liquid pipe line communicating with the second insertion passage, the gripping cylinder is an integrally molded body in which the first connecting pipe and the second connecting pipe are integrally molded, the gripping cylinder side portion has a flange-shaped stopper formed to extend outward from an inside in a radial direction of a center axis of the gripping cylinder, and the first position and the second position are positions on the stopper or between the proximal end of the gripping cylinder and the stopper, wherein in a case where a plane orthogonal to the center axis of the gripping cylinder is defined as a first surface, and a plane orthogonal to the first surface and intersecting the air supply pipe line is defined as a second surface, the first position and the second position are disposed on the same side with respect to a reference surface orthogonal to the first surface and orthogonal to the second surface, wherein an angle of a pipe line axis of the gas pipe line with respect to the reference surface is different from an angle of a pipe line axis of the liquid pipe line with respect to the reference surface.

20. The overtube according to claim 19, wherein in the gas pipe line and the liquid pipe line of the gripping cylinder, the gas pipe line is disposed at a position outside the liquid pipe line with respect to the center axis of the gripping cylinder.

* * * * *